United States Patent
Jung et al.

(10) Patent No.: US 9,881,125 B2
(45) Date of Patent: *Jan. 30, 2018

(54) ULTRASOUND MEASUREMENT OF BIOMETRICS OF FETUS

(71) Applicant: SAMSUNG ELECTRONICS CO., LTD., Suwon-si (KR)

(72) Inventors: Hae-kyung Jung, Seoul (KR); Hee-chul Yoon, Seoul (KR); Hyun-taek Lee, Seoul (KR); Yong-je Kim, Yongin-si (KR); Jae-hyun Kim, Seoul (KR); Myung-jin Eom, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 516 days.

This patent is subject to a terminal disclaimer.

(21) Appl. No.: 13/734,217

(22) Filed: Jan. 4, 2013

(65) Prior Publication Data
US 2013/0173175 A1  Jul. 4, 2013

(30) Foreign Application Priority Data
Jan. 4, 2012 (KR) ............ 10-2012-0001150

(51) Int. Cl.
*G06F 19/26* (2011.01)
*A61B 8/08* (2006.01)
*A61B 8/00* (2006.01)

(52) U.S. Cl.
CPC ............ *G06F 19/26* (2013.01); *A61B 8/0866* (2013.01); *A61B 8/5223* (2013.01); *A61B 8/085* (2013.01); *A61B 8/0858* (2013.01); *A61B 8/469* (2013.01)

(58) Field of Classification Search
None
See application file for complete search history.

(56) References Cited

U.S. PATENT DOCUMENTS

| 5,605,155 A | 2/1997 | Chalana et al. |
| 5,605,166 A | 2/1997 | Chou |
| 7,796,790 B2 | 9/2010 | McNutt et al. |
| 2002/0102023 A1 | 8/2002 | Yamauchi |
| 2011/0282199 A1 | 11/2011 | Lee et al. |

FOREIGN PATENT DOCUMENTS

| EP | 0 916 308 A1 | 5/1999 |
| EP | 2 387 949 A1 | 11/2011 |
| JP | 2003-216959 A | 7/2003 |
| JP | 2006-288964 A | 10/2006 |

(Continued)

OTHER PUBLICATIONS

Snijders, "UK multicentre project on assessment of risk of trisomy 21 by maternal age and fetal nuchal-translucency thickness at 10-14 weeks of gestation," Lancet, vol. 352, p. 343-346, 1998.*

(Continued)

*Primary Examiner* — G. Steven Vanni
(74) *Attorney, Agent, or Firm* — Sughrue Mion, PLLC

(57) ABSTRACT

A method for measuring biometrics of an object includes receiving an image of an object, modeling the object to identify a portion of the object, and measuring biometrics of the object based on a modeling result the object.

23 Claims, 13 Drawing Sheets

(56) References Cited

FOREIGN PATENT DOCUMENTS

| JP | 2007-508094 A | 4/2007 |
|---|---|---|
| JP | 2008-183063 A | 8/2008 |
| JP | 2010-187987 A | 9/2010 |
| JP | 2011-240132 A | 12/2011 |
| WO | 2009/136332 A2 | 11/2009 |

OTHER PUBLICATIONS

Whitlow, "The effect of fetal neck position on nuchal translucency measurement," British Journal of Obstetrics and Gynaecology, vol. 105, p. 872-876, 1998.*
Jardim, "Segmentation of fetal ultrasound images," Ultrasound in medicine & biology, vol. 31(2), p. 243-250, 2005.*
Communication dated Jun. 19, 2014 by the Chinese Patent Office in counterpart Chinese Patent Application No. 201310003303.4.
Communication, dated May 6, 2013, issued by the European Patent Office in counterpart European Patent Application No. 13150331.0.
Lee, Yu-Bu, et al., "Robust border enhancement and detection for measurement of fetal nuchal translucency in ultrasound images," International Federation for Medical and Biological Engineering, Medical and Biological Engineering and Computing, vol. 45, No. 11, Jul. 27, 2007, pp. 1143-1152.
Communication dated Apr. 8, 2014 issued by the Japanese Patent Office in counterpart Japanese Patent Application No. 2012-285606.
Communication from the Taiwanese Patent Office dated Feb. 11, 2015 in a counterpart Taiwanese application No. 102100140.

* cited by examiner

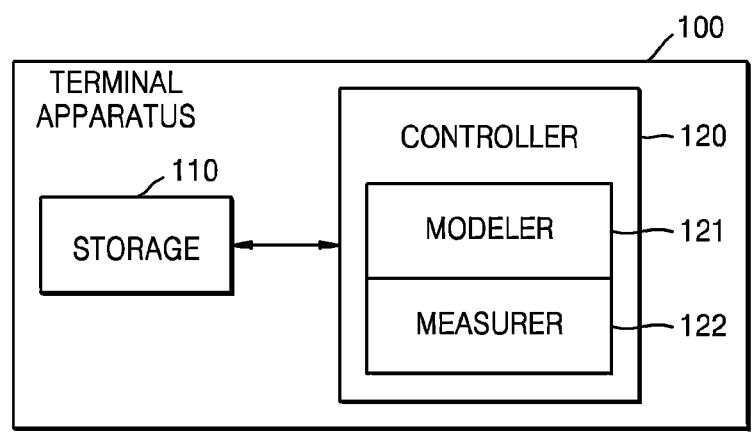
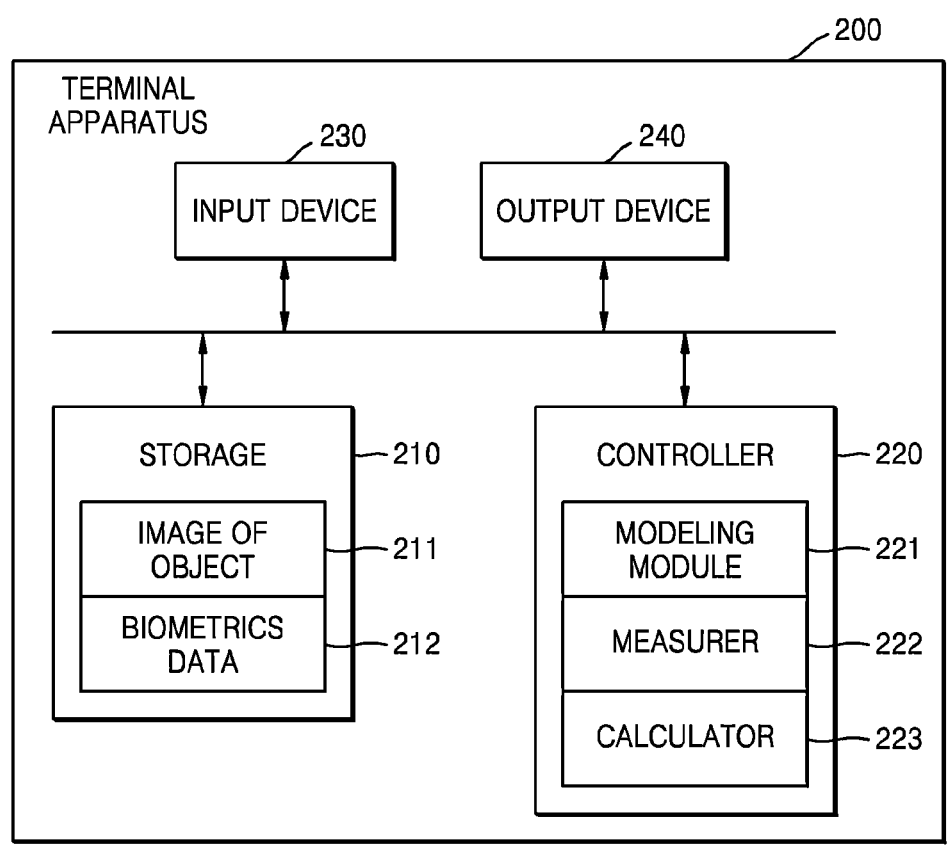

ULTRASOUND MEASUREMENT OF BIOMETRICS OF FETUS

CROSS-REFERENCE TO RELATED PATENT APPLICATION

This application claims the priority from Korean Patent Application No. 10-2012-0001150, filed on Jan. 4, 2012, in the Korean Intellectual Property Office, the disclosure of which is incorporated herein in its entirety by reference.

BACKGROUND

1. Field

Apparatuses and methods consistent with exemplary embodiments relate to measuring biometrics of an object from an ultrasound image of the object.

2. Description of the Related Art

Ultrasound systems have noninvasive and nondestructive characteristics and thus have been widely used in the medical field to obtain information about the internal portions of an object. The ultrasound systems provide a high-resolution image of an object in real time without a need to perform a surgical operation. Thus, the ultrasound systems have drawn much attention in the medical field.

Ultrasound images have been used for early diagnosis to determine whether a fetus has a defect in its chromosome or nervous system, e.g., Down syndrome. In order for a diagnostician to accurately measure biometrics of the fetus and diagnose a state of the fetus by determining the location of the fetus with the naked eyes, an image of a mid-sagittal plane of the fetus is detected and a fetal crown-rump length (CRL), a nuchal translucency (NT), and an intracranial translucency (IT) of the fetus are measured based on the image.

Although biometrics, such as the CRL, NT, and IT, are individually measured and output, a relative difference between the NT and the CRL or the IT and the CRL, i.e., a value calculated based on at least two biometrics is used to diagnose the state of the fetus. Thus, there is a need to automatically provide a user with a value calculated based on a result of integrating the biometrics, such as the CRL, NT, and IT, and a result of diagnosing the fetus based on the calculated value so that the user may easily diagnose and determine the state of the fetus.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

One or more exemplary embodiments provide a method and apparatus for automatically measuring biometrics of an object by using an ultrasound image of the object.

According to an aspect of an exemplary embodiment, there is provided a method of measuring biometrics of an object, the method including receiving an image of the object, modeling the object such that at least one part of the object is identified, and measuring biometrics of the object, based on a result of modeling the object.

The modeling of the object may include displaying a result of modeling the at least one part of the object in an oval shape including a circular shape, and modifying the result of modeling the object, based on a user input signal.

The measuring of the biometrics of the object may include determining whether the measured biometrics fall within a normal range, modeling the object again by estimating a case where the biometrics fall within the normal range when it is determined that the measured biometrics do not fall within the normal range, and measuring the biometrics of the object again, based on the estimated modeling result.

The measuring of the biometrics of the object may include detecting a region-of-interest (ROI) for measuring the biometrics, based on the result of modeling the object; and measuring the biometrics in the ROI.

The detecting of the ROI may include displaying the detected ROI to be differentiated from the other parts of the object, displaying a region for measuring the biometrics, in the ROI, and modifying the ROI or the region for measuring the biometrics, according to a user input signal.

The modeling of the object may include modeling the object such that a body and head of the object are identified.

After the modeling of the object, the method may further include detecting at least one characteristic point on the head of the object, setting a central axis by using the at least one characteristic points and then displaying the central axis, measuring an angle between the body and head of the object with respect to the central axis, determining whether the angle falls within a normal range, and measuring a crown-rump length (CRL) of the object, based on a result of the determining.

The measuring of the CRL may include measuring the CRL of the object based on the result of modeling the object when the angle falls within the normal range, estimating a result of modeling the object when the angle falls within the normal range when the angle does not fall within the normal range and then measuring the CRL of the object, based on the estimated modeling result, and displaying the estimated modeling result and the measured CRL.

The measuring of the biometrics may include measuring a crown-rump length (CRL) of the object, measuring at least one among a nuchal translucency (NT) and an intracranial translucency (IT) of the object, calculating a relative difference between the CRL and the NT or the IT, and displaying the measured CRL, NT, and IT.

According to another aspect of an exemplary embodiment, there is provided a terminal apparatus for measuring biometrics of an object, the terminal apparatus including a storage for storing an image of the object, and a controller. The controller includes a modeler for modeling the object such that at least one part of the object is identified in the image of the object; and a measurer for measuring biometrics of the object, based on a result of modeling the object.

The terminal apparatus may further include an input device for receiving a user input. The modeler may modify the result of modeling the object, based on a user input signal.

The storage may store biometrics data including information about a normal range of at least one of biometrics. If the measured biometrics do not fall within the normal range, the modeler may model the object again by estimating a case where the biometrics fall within the normal range. If the measured biometrics do not fall within the normal range, the measurer may measure the biometrics of the object again, based on the estimated modeling result.

The controller may further include a calculator for calculating an error rate between a result of measuring the biometrics again and the biometrics measured using the result of modeling the object.

The measurer may detect a region-of-interest (ROI) for measuring the biometrics, based on the result of modeling the object, and measure the biometrics in the ROI. The terminal apparatus may further include an output device for outputting the detected ROI to be differentiated from the other parts of the object, and output a region for measuring the biometrics in the ROI.

The terminal apparatus may further include an input device for receiving a user input. The measurer may modify the ROI according to a user input signal.

The modeler may model the object such that a body and head of the object are identified.

The modeler may detect at least one characteristic point on the head of the object, and set a central axis by using the at least one characteristic point.

The storage may store biometrics data including information about a normal range of at least one of biometrics. The measurer may measure an angle between the body and head of the object, determine whether the angle falls within a normal range, and measure a crown-rump length (CRL) of the object, based on a result of the determining. The terminal apparatus may further include an output device for outputting a result of estimating a result of modeling the object when the angle fall within a normal range and a result of measuring the CRL of the object.

If the angle falls within the normal range, the measurer may measure the CRL of the object based on the result of modeling the object. If the angle does not fall within the normal range, the measurer may estimate a result of modeling the object when the angle falls within the normal range, and measure the CRL of the object based on the estimated modeling result.

The measurer may measure the CRL of the object, and measure at least one among a nuchal translucency (NT) and an intracranial translucency (IT) of the object. The controller may further include a calculator for calculating a relative difference between the CRL and the NT or IT.

The controller may provide a user interface via which after modeling the object or extracting a region for measuring the biometrics of the object is automatically performed, whether a result of modeling the object or the extracted region is set to be verified by a user, according to a user input signal.

The controller may provide a user interface via which whether at least one among modeling the object, extracting a region for measuring the biometrics of the object, and estimating a result of modeling the object is to be performed automatically or manually, is set according to a user input signal.

BRIEF DESCRIPTION OF THE DRAWINGS

The above and/or other aspects will become more apparent by describing certain exemplary embodiments with reference to the accompanying drawings, in which:

FIG. 1 is a block diagram of a terminal apparatus that measures biometrics of an object, according to an exemplary embodiment FIG. 2 is a block diagram of a terminal apparatus that measures biometrics of an object, according to an exemplary embodiment;

DETAILED DESCRIPTION

Figure 3:
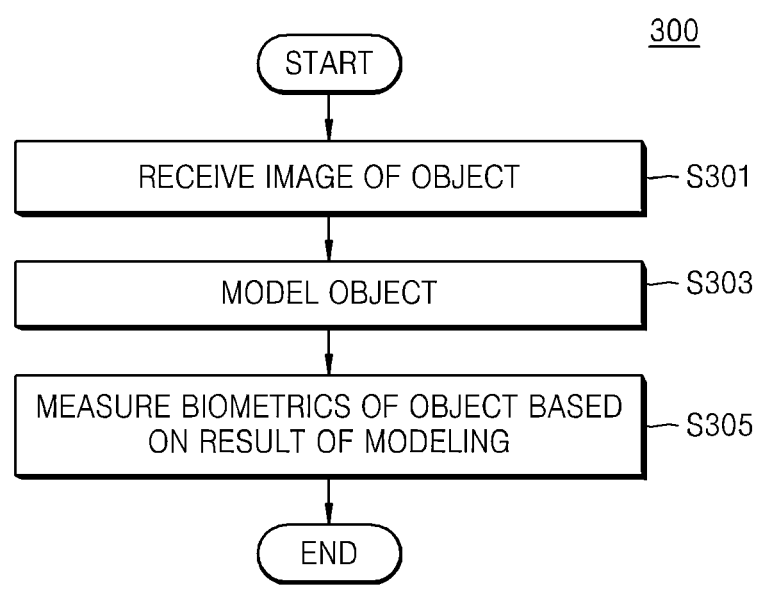
FIG. 3 is a flowchart illustrating a method of measuring biometrics of an object, according to an exemplary embodiment.

Certain exemplary embodiments are described in greater detail below, with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein. Although few exemplary embodiments are described, it would be appreciated by those of ordinary skill in the art that changes may be made in these exemplary embodiments without departing from the principles and spirit of the invention, the scope of which is defined in the claims and their equivalents.

As used herein, 'at least one of,' when preceding a list of elements, modify the entire list of elements and does not modify the individual elements of the list.

FIG. 1 is a block diagram of a terminal apparatus 100 that measures biometrics of an object, according to an exemplary embodiment. The terminal apparatus 100 of FIG. 1 may be similar to a terminal apparatus 200 of FIG. 2 which will be described below.

Biometrics may include length information of a human body, for example, a crown-rump length (CRL), an intracranial translucency (IT), and a nuchal translucency (NT) of a fetus. According to an exemplary embodiment, a state of an object may be diagnosed by measuring biometrics of the object, based on an image of the object.

Referring to FIG. 1, the terminal apparatus 100 according to an exemplary embodiment may include a storage 110 and a controller 120.

The terminal apparatus 100 may be included as an element of an image analysis apparatus included in a medical image diagnosis apparatus, e.g., an X-ray apparatus, an ultrasound apparatus, a computed tomography (CT) apparatus, or magnetic resonance imaging (MRI) apparatus. Otherwise, the terminal apparatus 100 may be any of various apparatuses that a user uses, e.g., a personal computer (PC), a notebook computer, a mobile phone, a tablet PC, a navigation system, a smart phone, a personal digital assistant (PDA), a smart television (TV), a portable multimedia player (PMP), and a digital broadcasting receiver. In addition, the terminal apparatus 100 should be understood as a concept including all other apparatuses that are currently developed and placed on the market or that are to be developed in the future.

According to an exemplary embodiment, the storage 110 stores data or a program for operating the terminal apparatus 100. Basically, the storage 110 may store an operating system (OS) of the terminal apparatus 100, at least one application program, and an image of the object. The image of the object may include an internal or external image of the object for measuring biometrics of the object, such as an ultrasound image, an MRI image, a CT image, or an X-ray image. The storage 110 may be any of various storage media, e.g., a random access memory (RAM), a read-only memory (ROM), a hard disk drive (HDD), a flash memory, a compact disc (CD)-ROM, and a digital versatile disc (DVD).

The controller 120 controls operations of the terminal apparatus 100. Basically, the controller 120 operates based on the OS stored in the storage 110 to build a basic platform environment of the terminal apparatus 100, and runs an application program to provide a desired function according to a user's selection.

Specifically, the controller 120 may control such that an image of the object is received from an external device (not shown) or the storage 110, the object is modeled to identify respective object regions based on the image of the object, biometrics of the object are measured based on a result of modeling the object, and the measured biometrics and the result of modeling the object are then output to an external display unit (not shown) or an output device (not shown) included in the terminal apparatus 100.

According to an exemplary embodiment, the controller 120 may include a modeler 121 and a measurer 122.

The modeler 121 models the object such that the respective regions of the object may be identified, based on the image of the object. The object may be modeled in an oval shape including a circular shape, but is not limited thereto. If the object is a fetus, the head and body of the fetus may be modeled in a circular or oval shape to be differentiated from each other and a result of modeling the object may be output via an output device.

The measurer 122 measures biometrics of the object based on the result of modeling the object when the modeler 121 models the object such that the respective regions of the object are identified. If the object is a fetus, then a central axis may be set on the circular or oval shape with which the object is modeled, based on characteristic points of the head and body of the fetus. The CRL, NT, and IT biometrics of the fetus may be measured based on the set central axis.

FIG. 2 is a block diagram of a terminal apparatus 200 that measures biometrics of an object, according to an exemplary embodiment.

Referring to FIG. 2, the terminal apparatus 200 according to an exemplary embodiment may include a storage 210, a controller 220, an input device 230, and an output device 240. The storage 210 and the controller 220 correspond to the storage 110 and the controller 120, respectively, and are not described again here.

According to an exemplary embodiment, there is provided a method of measuring biometrics, which is capable of increasing the accuracy of biometrics by determining whether the biometrics fall within a normal range, i.e., a range pre-specified by a user based on certain criteria.

According to an exemplary embodiment, the storage 210 may store an image 211 of the object, and biometrics data 212. The storage 210 may store the biometrics data 212 including information about the normal range of the biometrics to determine whether measured biometrics fall within the normal range.

According to an exemplary embodiment, the controller 220 may include a modeler 221, a measurer 222, and a calculator 223.

When biometrics measured by the measurer 222 do not fall within the normal range, the modeler 221 may calculate a model of the object by estimating a new model so that the biometrics fall within the normal range.

When the biometrics measured by the measurer 222 do not fall within the normal range, the measurer 222 measures biometrics of the object, based on the estimated modeling result.

When the biometrics measured by the measurer 222 do not fall within the normal range and the object is modeled by estimating a case where the biometrics fall within the normal range, the calculator 223 may calculate an error rate between biometrics measured again by the measurer 222 and the previously measured biometrics.

The input device 230 is a unit that generates a user input signal for controlling or operating the terminal apparatus 200, under a user's manipulation, and may include various input devices. For example, the input device 230 may include at least one among a key input device, a touch input device, a gesture input device, a voice input device, and the like. The key input device may generate a signal corresponding to a key when the key is manipulated, and may be a keypad or a keyboard. The touch input device may recognize a user input by sensing a user's touch on a particular part, and may be a touch pad, a touch screen, or a touch sensor. The gesture input device senses a user's predetermined motion, e.g., shaking or moving a terminal, accessing the terminal, or blinking of the user's eyes, as a particular input signal, and may include at least one among a terrestrial magnetism sensor, an acceleration sensor, a camera, an altimeter, a gyro sensor, and a proximity sensor.

The output device 240 outputs a user interface for providing biometrics and a result of measuring to a screen (not shown) of the terminal apparatus 200. For example, the output device 240 may be one of a liquid crystal display (LCD), a thin film transistor-LCD (TFT-LCD), light-emitting diodes (LEDs), organic light-emitting diodes (OLEDs), active matrix organic light-emitting diodes (AMOLED), a flexible display, and a three-dimensional (3D) display.

FIG. 3 is a flowchart illustrating a method 300 of measuring biometrics of an object, according to an exemplary embodiment.

The method 300 of FIG. 3 may be performed by the terminal apparatus 100 of FIG. 1 or the terminal apparatus 200 of FIG. 2.

The method 300 performed by the terminal apparatus 100 or 200 will now be described in detail.

The terminal apparatus 100 or 200 may receive an image of an object from an external storage device or may read an image stored in the storage 110 to measure biometrics of the object, according to a request from a user or a control signal (operation S301). The receiving or reading of the image in operation S301 may be performed by the controller 120 or 220.

The object is modeled based on the image received or read in operation S301 such that at least one part of the object may be identified (operation S303). Operation S303 may be performed by the modeler 121 or 221.

Biometrics of the object may be measured based on a result of modeling the object performed in operation S303 (operation S305).

Operation S305 may be performed by the measurer 122 or 222.

The result of modeling the object may be output to a user, and the user may view and modify the result of modeling the object.

Figure 4:
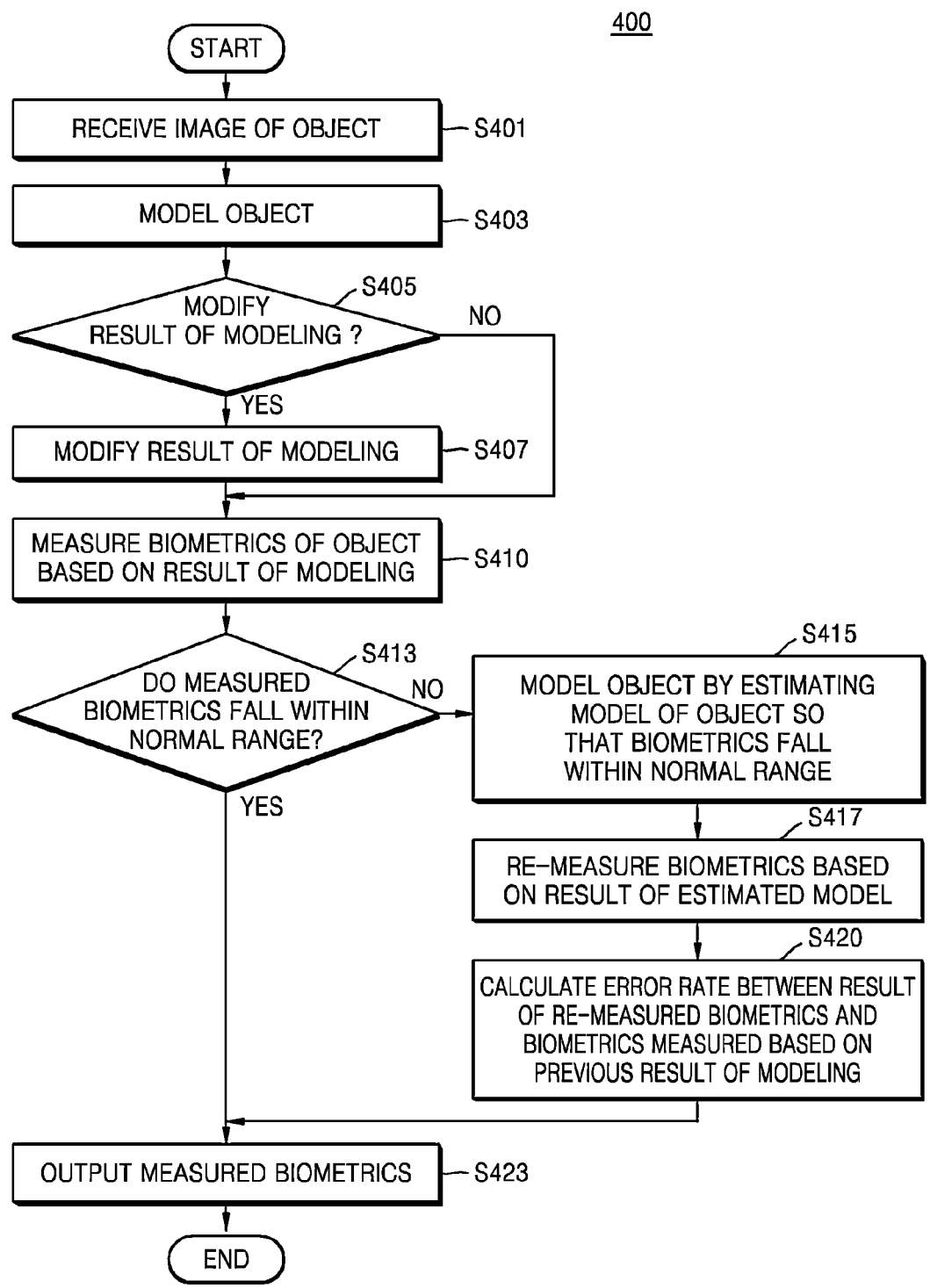
FIG. 4 is a flowchart illustrating a method of measuring biometrics of an object, according to an exemplary embodiment.

FIG. 4 is a flowchart illustrating a method 400 of measuring biometrics of an object, according to an exemplary embodiment.

The method 400 of FIG. 4 may be performed by the terminal apparatus 200 of FIG. 2 as described in detail below.

The terminal apparatus 200 may receive an image of an object from an external storage device or read the image 211 of the object stored in the storage 210 to measure biometrics of the object, according to a request from a user or a control signal (operation S401). In operation S401, the receiving of the image or the reading of the image 211 may be performed by the controller 220.

Then, the object may be modeled such that at least one part of the object may be identified, based on the image 211 of the object (operation S403). Operation S403 may be performed by the modeler 221.

A result of modeling the object may be output to a user via the output device 240, and the user may view and modify the result of modeling the object, i.e., the object model. If it is determined that the user checks the result of modeling the object and requests to modify the result of modeling the object, and the result of modeling the object may be modified as requested by the user (operation S407). The request to modify the result of modeling the object in operation S405 may be received via the input device 230, and operation S407 may be performed by the controller 220.

If it is determined that the user does not request to modify the result of modeling the object (operation S405), biometrics of the object may be measured based on the result of modeling the object (operation S410). In operation 413, it is determined whether the measured biometrics fall within a normal range based on the biometrics data 212 stored in the storage 210 of the terminal apparatus 200 (operation S413). If the measured biometrics do not fall within the normal range, the accuracy of the measured biometrics may be determined to be low.

Otherwise, if the measured biometrics fall within the normal range, the measured biometrics are output (operation S423). If the measured biometrics do not fall within the normal range, the object may be modeled again by estimating a case where the biometrics fall within the normal range (operation S415). Biometrics of the object are re-measured based on the estimated modeling result (operation S417). The biometrics measured again and the biometrics measured based on the previous result of modeling the object are compared to calculate an error rate therebetween (operation S420).

The terminal apparatus 200 may calculate and output data for diagnosing a state of the object, based on the measured biometrics. If the measured biometrics do not fall within the normal range, the accuracy of the measured biometrics may be determined to be low. Thus, the data for diagnosing the state of the object may be calculated and output, based on the biometrics measured based on the estimated modeling result.

Figure 5:
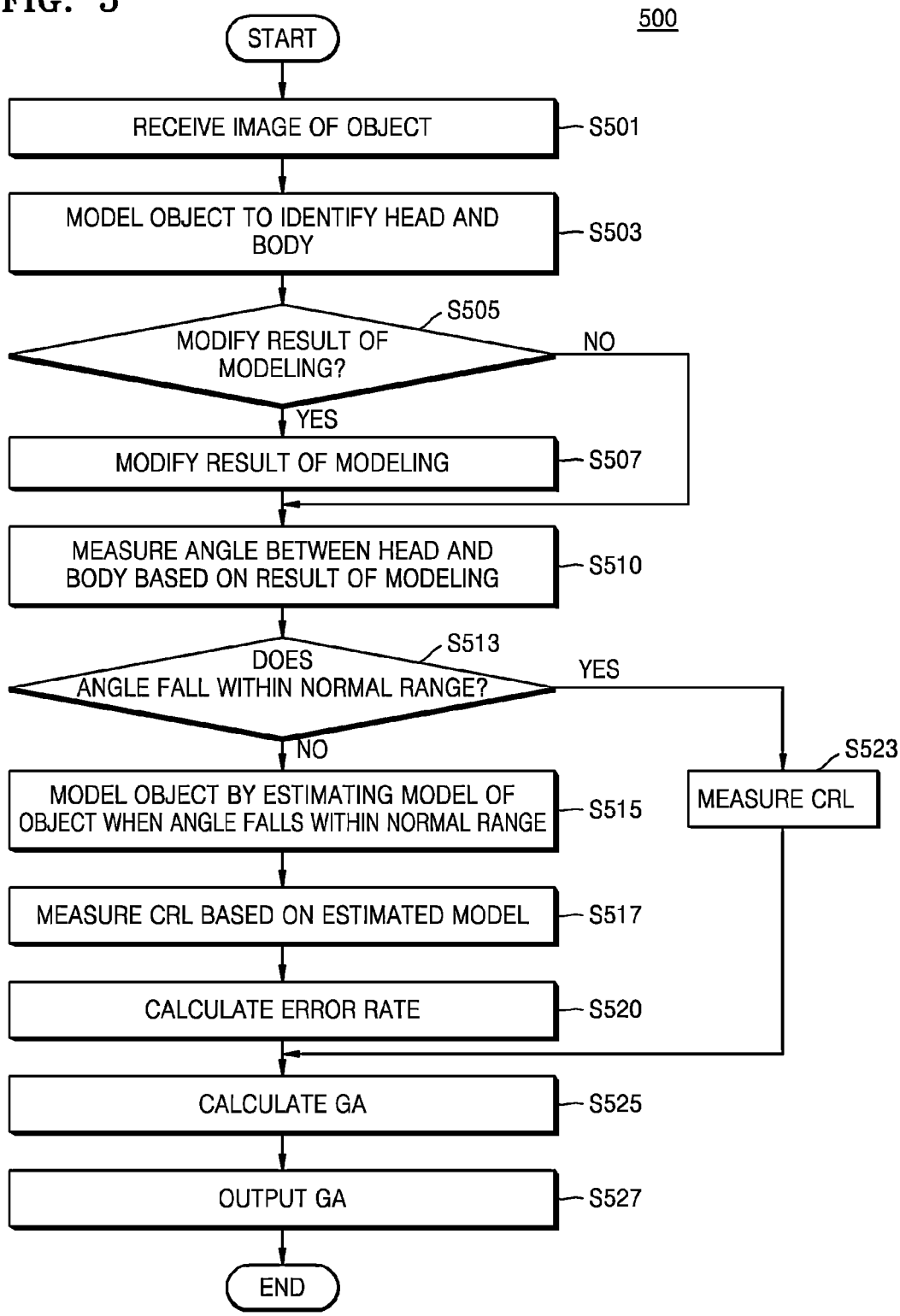
FIG. 5 is a flowchart illustrating a method of measuring a crown-rump length (CRL) of an object, according to an exemplary embodiment.

FIG. 5 is a flowchart illustrating a method 500 of measuring a CRL of an object, according to an exemplary embodiment According to an exemplary embodiment, the object is modeled such that a head and a body of the object may be identified to measure the CRL of the object, which is one of biometrics. Modeling of the object may be estimated and performed again to increase the accuracy of measured biometrics, according to whether an angle between the head and body of the object falls within a normal range.

The terminal apparatus 200 of FIG. 2 may receive an image of an object from an external device or may read the image 211 of the object stored in the storage 210 to measure biometrics of the object, according to a request from a user or a control signal (operation S501).

The object may be modeled such that the head and body of the object may be identified, based on the image 211 of the object (operation S503). A result of modeling the object may be output to a user via the output device 240, and the user may check the result of modeling the object. In operation S505, it is determined whether the user requests to modify the result of modeling the object, and the result of modeling the object may be modified as requested by the user (operation S507).

A CRL of the object may be measured based on the result of modeling the object. First, characteristic points of the head and body of the object may be extracted, and a central axis may be set on a figure obtained by modeling the object, based on the extracted characteristic points. An angle between the head and body of the object may be measured based on the central axis (operation S510). Here, the characteristic points may represent a predetermined portion of the object, including at least one of the crown of the head, palatine bones, and the end of a nose of the object.

If the angle between the head and body of the object falls within the normal range, then the CRL of the object may be accurately measured. In the case of a fetus, for example, the CRL may be measured to be small when the fetus crouches down to a large extent, and may be measured to be too large when the fetus stretches. Thus, the measured CRL may not appropriate to be used to calculate a gestational age (GA), which is a value for diagnosing a state of the fetus.

In operation 513, whether the angle falls within the normal range may be determined based on information about the normal range of the angle, included in the biometrics data 212 stored in the storage 210 of the terminal apparatus 200, thereby enabling the CRL to be accurately measured.

If the angle falls within the normal range, the CRL is measured using the result of modeling the object (operation S523). Otherwise, if the angle does not fall within the normal range, the object is modeled again by estimating a case where the angle falls within the normal range (operation S515). In the case of a fetus, for example, when the angle between the head and body of the object does not fall within the normal range since the fetus crouches down to a large extent, modeling of the object may be estimated and performed again by controlling the figure obtained by modeling the object such that the central axis on the head or body may be moved to a side.

The CRL is re-measured based on the estimated modeling result (operation S517). A result of re-measuring the CRL based on the estimated modeling result and a result of measuring the CRL based on the previous result of modeling the object are compared to calculate an error rate therebetween (operation S520).

Thereafter, a GA, which is a value for diagnosing a state of the fetus, may be calculated based on the CRL (operation S525), and may then be output via the output device 240 (operation S527).

Figure 6:
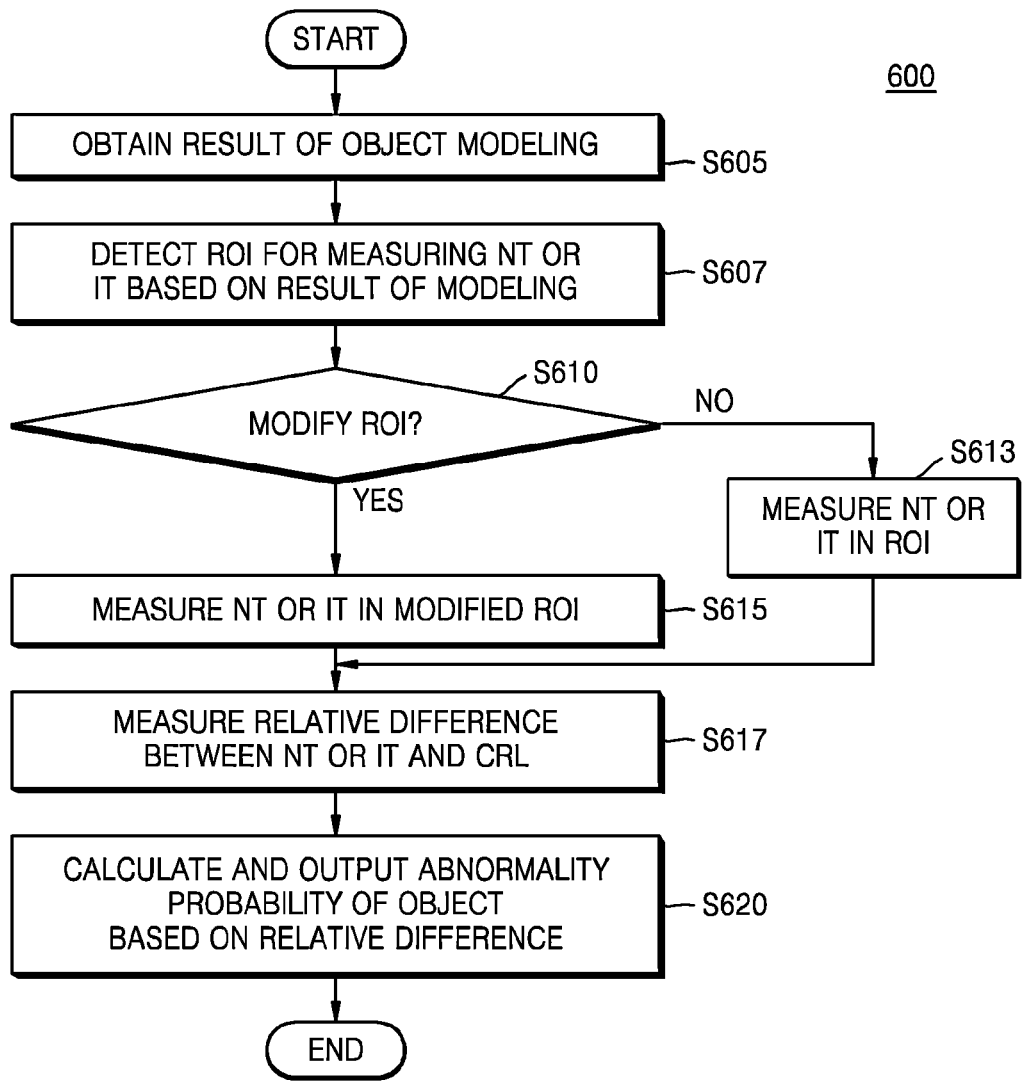
FIG. 6 is a flowchart illustrating a method of measuring a nuchal translucency (NT) or an intracranial translucency (IT) of an object, according to an exemplary embodiment.

FIG. 6 is a flowchart illustrating a method 600 of measuring an NT or an IT of an object, according to an exemplary embodiment.

In an exemplary embodiment, the IT or the NT of the object may be measured based on a result of modeling the object. The object may be modeled such that a head and body of the object may be identified as described above, and the IT or NT of the object may then be measured. In this case, measuring of the CRL may be optional. Thus, in operation S605, a model of the object may be obtained as a result of operation S507 and/or S505 of FIG. 5.

Referring to FIG. 6, the location of the NT or IT of the object may be estimated based on the result of modeling the object. In the case of a fetus, the NT is the nape and may thus be estimated as a region in which the head and body intersect. The IT is located in the skull and may thus be estimated to be located in a region in which a central point and a central axis on the head intersect. A region-of-interest (ROI) in which the NT or IT may be measured may be indicated.

A region in which the NT or IT may be measured, i.e., the ROI, may be detected and output based on the result of modeling the object (operation S607). A user may check the output ROI and request to modify the ROI.

In operation S610, if it is determined that the request to modify the ROI from the user is not received, the controller 220 may measure the NT or IT in the ROI (operation S613).

Otherwise, if the controller 220 receives the request to modify the ROI from the user, the controller 220 may modify the ROI based on the request from the user and may measure the NT or IT in the modified ROI (operation S615).

The NT and IT are measured as lengths and may thus be displayed in the form of a line, together with the ROI.

When the NT or IT is measured, a relative difference between the NT or IT and the CRL of the object is calculated (operation S617). An abnormality probability of the object may be calculated and output, based on the relative difference (operation S620). The relative difference may be expressed as NT/CRL or IT/CRL. The CRL has to be measured to calculate the relative difference between the CRL and the NT or IT. The CRL may be measured as described above.

Figure 7:
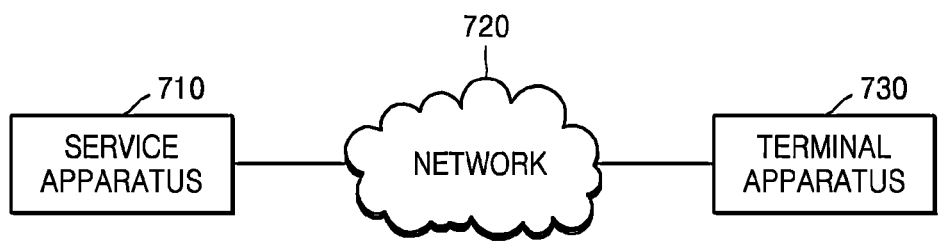
FIG. 7 is a block diagram of a system that measures biometrics of an object, according to an exemplary embodiment.

FIG. 7 is a block diagram of a system that measures biometrics of an object, according to an exemplary embodiment.

Referring to FIG. 7, the system may include a service apparatus 710, a network 720, and a terminal apparatus 730.

According to an exemplary embodiment, biometrics of an object may be measured and a state of the object may be diagnosed according to a computer-based method in which a device that is connected to the terminal apparatus 730 via the network 720 measures the biometrics of the object and diagnoses a state of the object, and only information is input to or output from the terminal apparatus 730. For convenience of explanation, a device that measures the biometrics of the object and diagnoses the state of the object, in response to a request from the terminal apparatus 730 according to exemplary embodiments may be hereinafter referred to as the service apparatus 710.

The service apparatus 710 measures the biometrics of the object based on an image of the object received via the network 720, and provides the terminal apparatus 730 with a result of the measuring and a result of diagnosing the state of the object based on the result of the measuring. More specifically, the object may be modeled such that at least one object portion may be identified in the image of the object, the biometrics of the object may be measured based on a result of modeling the object, a state of the object may be diagnosed according to a result of the measuring, and a result of the diagnosing may be provided to the terminal apparatus 730. The service apparatus 710 may provide a user interface via which the result of modeling the object and the measured biometrics may be provided to the terminal apparatus 730 so that a user may view, check, verify, and/or modify a process of measuring the biometrics of the object.

The service apparatus 710 may operate based on a server-client computing or a cloud computing and may include computer resources for measuring the biometrics of the object and diagnosing the state of the object, such as, for example, at least one of hardware and software.

The network 720 provides a path for exchanging data between the service apparatus 710 and the terminal apparatus 730. The network 720 is an internet protocol (IP) network via which a service for receiving/transmitting a large amount of data and a data service are provided by using an IP. The network 720 may be an all-IP network that is an IP network structure obtained by integrating different networks based on an IP. Also, the network 720 may include at least one of a 3G mobile network including a wired network, a wireless broadcasting (Wibro) network, a wideband code division multiple access (WCDMA) network, a 3.5G mobile network including a high-speed downlink packet access (HSDPA) network and a long-term evolution (LTE) network, a 4G mobile network including LTE advanced, and a wireless local area network (LAN) including a satellite network and a Wi-Fi network.

According to exemplary embodiments, the terminal apparatus 730 performs an operation of outputting the result of measuring the biometrics of the object and the result of diagnosing the state of the object, performed by the service apparatus 710, as described in detail below.

Figure 8:
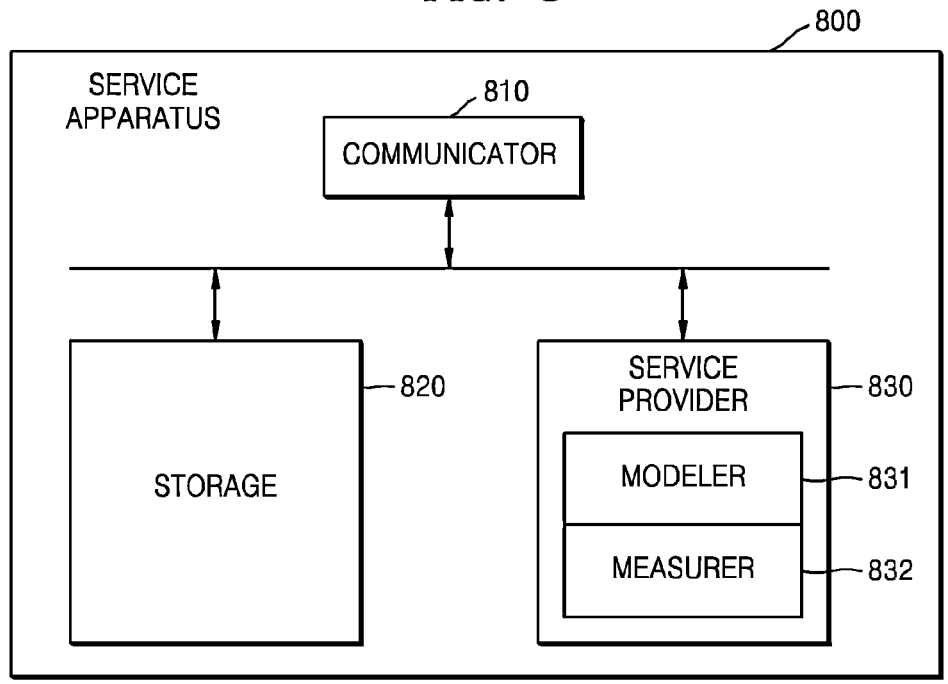
FIG. 8 is a block diagram of a service apparatus included in a system that measures biometrics of an object, according to an exemplary embodiment.

FIG. 8 is a block diagram of a service apparatus 800 included in a system that measures biometrics of an object, according to an exemplary embodiment. The service apparatus 800 of FIG. 8 may be similar to the service apparatus 710 of FIG. 7 or to a service apparatus 900 of FIG. 9.

Referring to FIG. 8, the service apparatus 800 may include a communicator 810, a storage 820, and a service provider 830.

The communicator 810 exchanges data with the terminal apparatus 730 of FIG. 7 via the network 720 of FIG. 7.

The storage 820 stores data and a program for operating the service apparatus 800. In an exemplary embodiment, the storage 820 may store an image of an object. The image of the object may include an internal or external image of the object for measuring biometrics of the object, e.g., an ultrasound image, an MRI image, a CT image, or an X-ray image of the object. The storage 820 may include various storage media, such as a RAM, a ROM, an HDD, a flash memory, a CD-ROM, and/or a DVD.

The service provider 830 may control the image of the object to be received from an external device (not shown) or the storage 820. The object may be modeled to identify at least one portion of the object, based on the image of the object. Biometrics of the object may be measured based on a result of modeling the object, and the measured biometrics may be then output to an external display unit (not shown) or an output device.

According to an exemplary embodiment, the service provider 830 may include a modeler 831 and a measurer 832.

The modeler 831 models the object such that respective regions of the object may be identified, based on the image of the object. The object may be modeled in an oval shape including a circular shape, but is not limited thereto. When the object is a fetus, the fetus may be approximately divided into a head and a body, and the head and body of the fetus may be modeled in a circular or oval shape and then be provided to an output device (not shown).

When the modeler 831 models the object to identify the respective object regions, the measurer 832 measures the biometrics of the object based on a result of modeling the object. If the object is a fetus, a central axis may be set on the circular or oval shape by using characteristic points of the head and body, and a CRL, NT, and IT of the fetus, which are biometrics, may be measured based on the set central axis.

Figure 9:
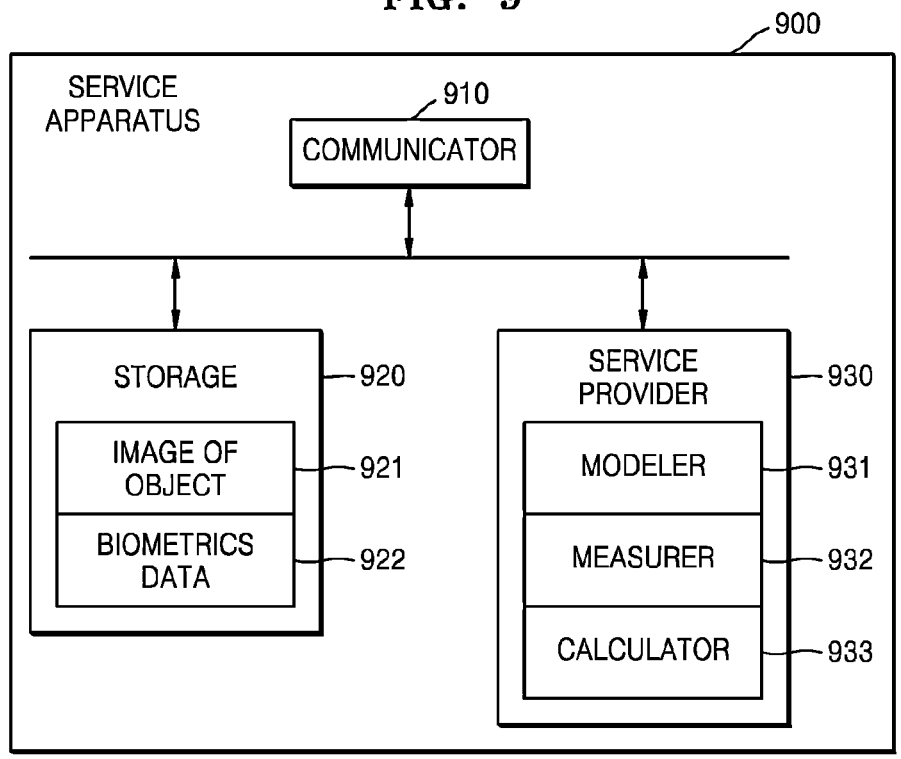
FIG. 9 is a block diagram of a service apparatus included in a system that measures biometrics of an object, according to an exemplary embodiment.

FIG. 9 is a block diagram of a service apparatus 900 included in a system that measures biometrics of an object, according to an exemplary embodiment.

Referring to FIG. 9, the service apparatus 900 according to an exemplary embodiment may include a communicator 910, a storage 920, and a service provider 930. The communicator 910, the storage 920, and the service provider 930 correspond to the communicator 810, the storage 820, and the service provider 830 of FIG. 8, respectively, and thus, repeated descriptions are not provided again.

According to an exemplary embodiment, the service apparatus 900 may provide a method of measuring biometrics of an object, which is capable of increasing the accuracy of biometrics by determining whether the biometrics fall within a normal range.

According to an exemplary embodiment, the storage 920 may store an image 921 and biometrics data 922 of an object. The storage 920 stores the biometrics data 922 including information about a normal range of at least one biometric, thereby enabling to determine whether measured biometrics fall within the normal range.

According to an exemplary embodiment, the service provider 930 may include a modeler 931, a measurer 932, and a calculator 933.

If biometrics measured by the measurer 932 do not fall within the normal range, the modeler 931 models the object again such that biometrics of the object may fall within the normal range.

If the measured biometrics do not fall within the normal range, the measurer 932 measures biometrics of the object again, based on a result of modeling the object again, performed by the modeler 931.

If the biometrics measured by the measurer 932 do not fall within the normal range and the object is modeled again by estimating a case where biometrics of the object fall within the normal range, the calculator 933 calculates an error rate between the biometrics measured again by the measurer 932 and the previously measured biometrics and provides the error rate to a user so that the user may determine the precision of the previously measured biometrics.

Figure 10:
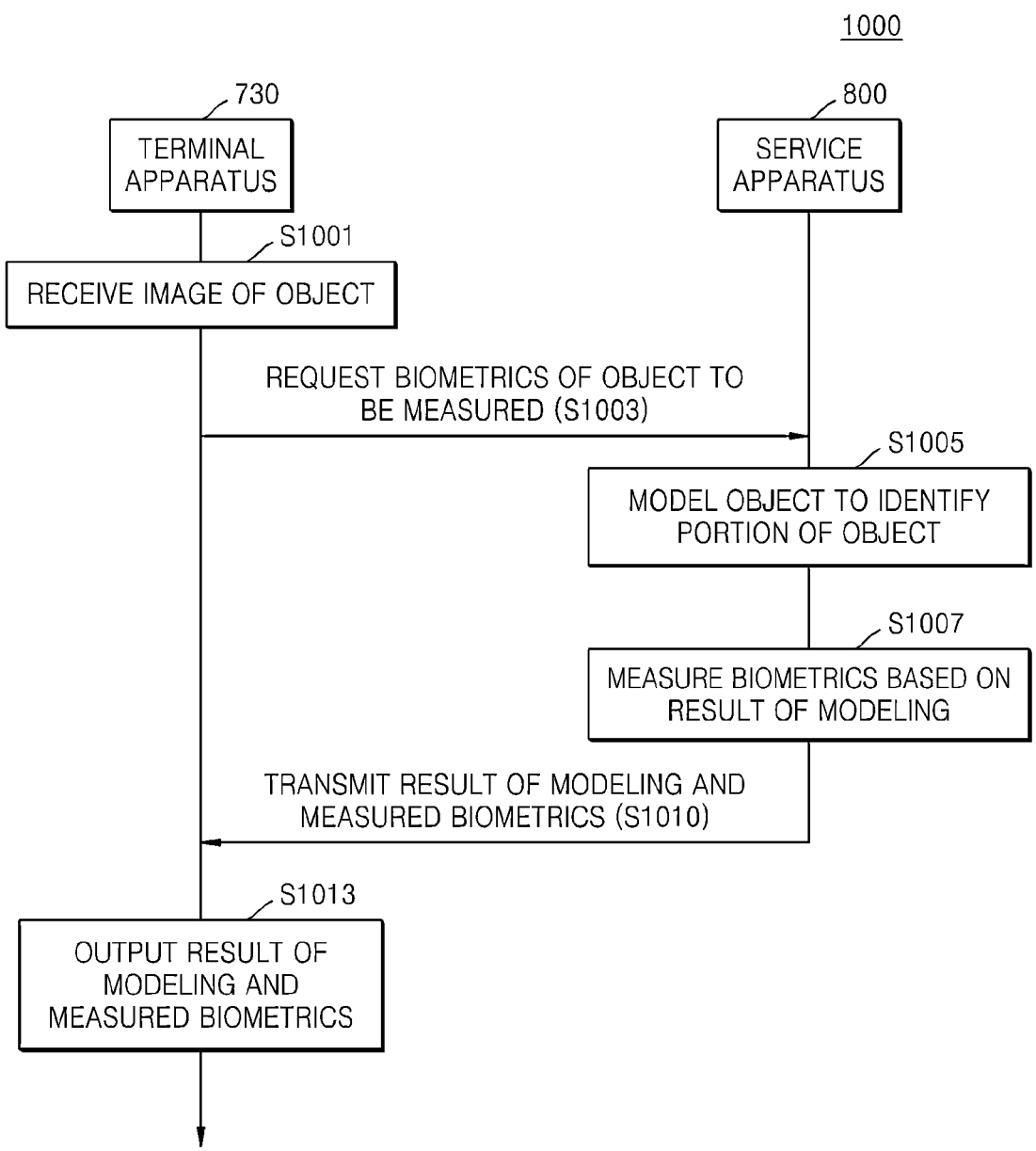
FIG. 10 is a flowchart illustrating a method of measuring biometrics of an object, according to an exemplary embodiment.

FIG. 10 is a flowchart illustrating a method 1000 of measuring biometrics of an object, according to an exemplary embodiment.

Referring to FIG. 10, a terminal apparatus 730 may receive an image of an object from an external device or may read an image stored in a storage to measure biometrics of the object, according to a request from a user or a control signal (operation S1001). The terminal apparatus 730 may transmit the image of the object to a service apparatus 800 to request to measure biometrics of the object (operation S1003). The image of the object may be stored in the service apparatus 800. The terminal apparatus 730 may request the service apparatus 800 to measure the biometrics of the object stored in the service apparatus 800 and provide the terminal apparatus 730 with a result of the measuring.

The service apparatus 800 may model the object such that at least one part of the object may be identified, based on the image of the object (operation S1005). The service apparatus 800 may measure biometrics of the object based on a result of modeling the object (operation S1007).

The result of modeling the object and the measured biometrics may be transmitted to the terminal apparatus 730 (operation S1010). The result of modeling the object and the measured biometrics may be output to the user via the terminal apparatus 730 (operation S1013). Thus, the user may view and modify the result of modeling the object and the measured biometrics.

Figure 11:
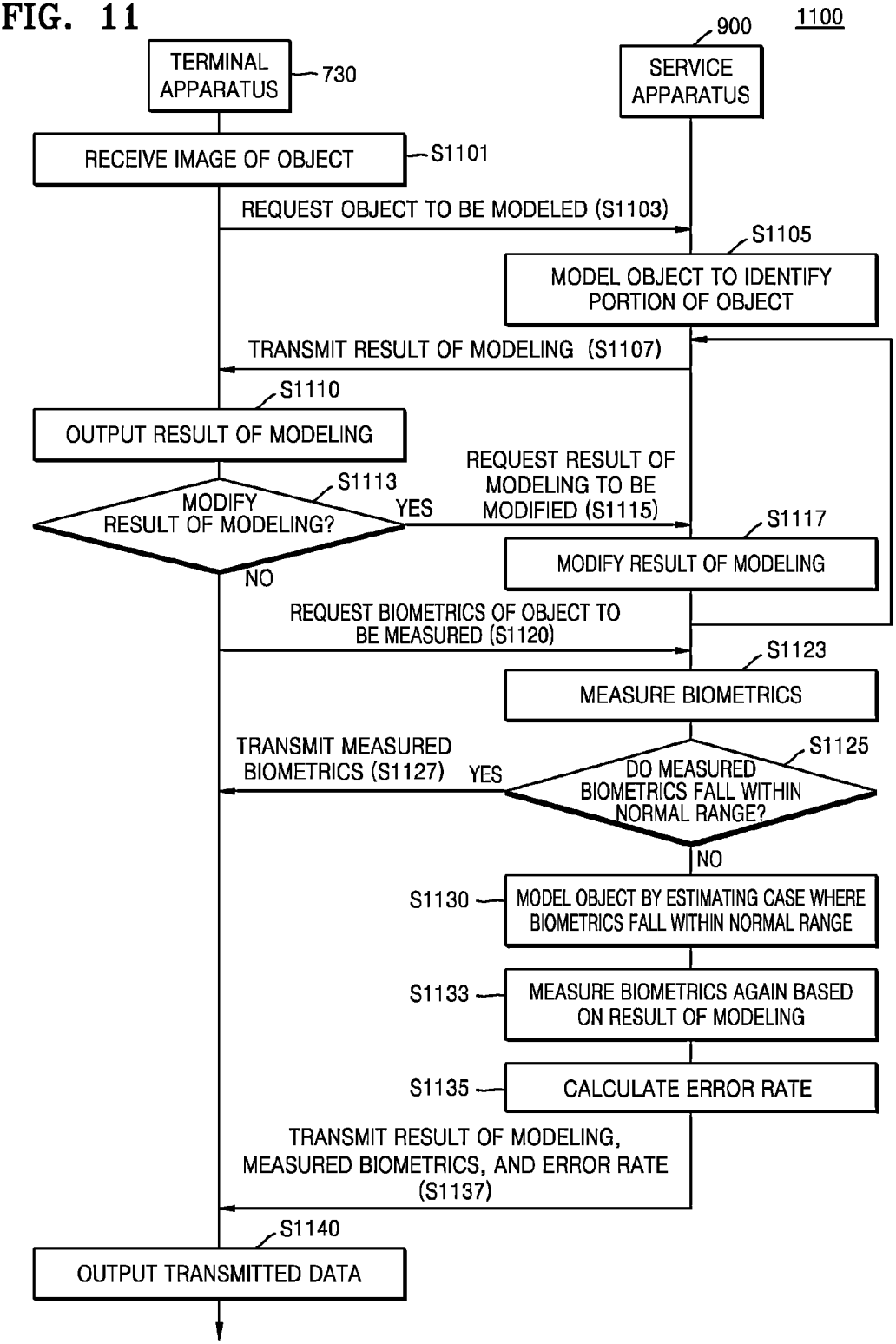
FIG. 11 is a flowchart illustrating a method of measuring biometrics of an object, according to an exemplary embodiment.

FIG. 11 is a flowchart illustrating a method 1100 of measuring biometrics of an object, according to an exemplary embodiment.

Referring to FIG. 11, a terminal apparatus 730 may receive an image of an object from an external device or may read an image stored in a storage to measure biometrics of the object, according to a request from a user or a control signal (operation S1101). The terminal apparatus 730 may transmit the image to a service apparatus 900 to request the service apparatus 900 to model the object in order to measure biometrics of the object (operation S1103). The image of the object may be stored in the service apparatus 900. The terminal apparatus 730 may request the service apparatus 900 to model the image of the object stored in the service apparatus 900.

The object may be modeled such that at least one part of the object may be identified, based on the image (operation S1105). A result of modeling the object may be transmitted to the terminal apparatus 730 (operation S1107). The result of modeling the object may be output to the user via the output device (not shown) in the terminal apparatus 730 (operation S1110). When the user views the result of modeling the object and requests the service apparatus 900 to modify the result of modeling the object, via an input device (not shown) of the terminal apparatus 730 (operations S1113 and S1115), the result of modeling the object may be modified as requested by the user (operation S1117).

When a request to modify the result of modeling the object is not received from the user, the service apparatus 900 may be requested to measure biometrics of the object (operation S1120). Then, the service apparatus 900 may measure biometrics of the object, based on the result of modeling the object (operation S1123).

Whether the measured biometrics fall within a normal range may be determined based on the biometrics data 922 stored in the storage 920 of the service apparatus 900 (operation S1125). If the measured biometrics do not fall within the normal range, the precision of the measured biometrics may be determined to be low.

Otherwise, if the measured biometrics fall within the normal range, the measured biometrics may be transmitted to the terminal apparatus 730 (operation S1127). The measured biometrics may be output to the user via the output device (not shown) in the terminal apparatus 730 (operation S1140). If the measured biometrics do not fall within the normal range, the object is modeled again by estimating a case where biometrics of the object fall within the normal range (operation S1130). The biometrics of the object are measured again based on a result of modeling the object again (operation S1133). The measured biometrics and the biometrics measured based on the previous result of modeling the object may be compared to calculate an error rate therebetween (operation S1135).

The service apparatus 900 may calculate data for diagnosing a state of the object from the measured biometrics and provide the data to the terminal apparatus 730. However, if the measured biometrics do not fall within the normal range, the precision of the measured biometrics may be determined to be low. Thus, the data for diagnosing the state of the object may be calculated from the biometrics measured based on the estimated modeling result, and then be provided to the terminal apparatus 730.

Thereafter, data related to the biometrics of the object, including the result of modeling the object, the measured biometrics, the error rate, and the like, may be transmitted to the terminal apparatus 730 (operation S1137). The data may be controlled to be output by the terminal apparatus 730 (operation S1140).

Figure 12:
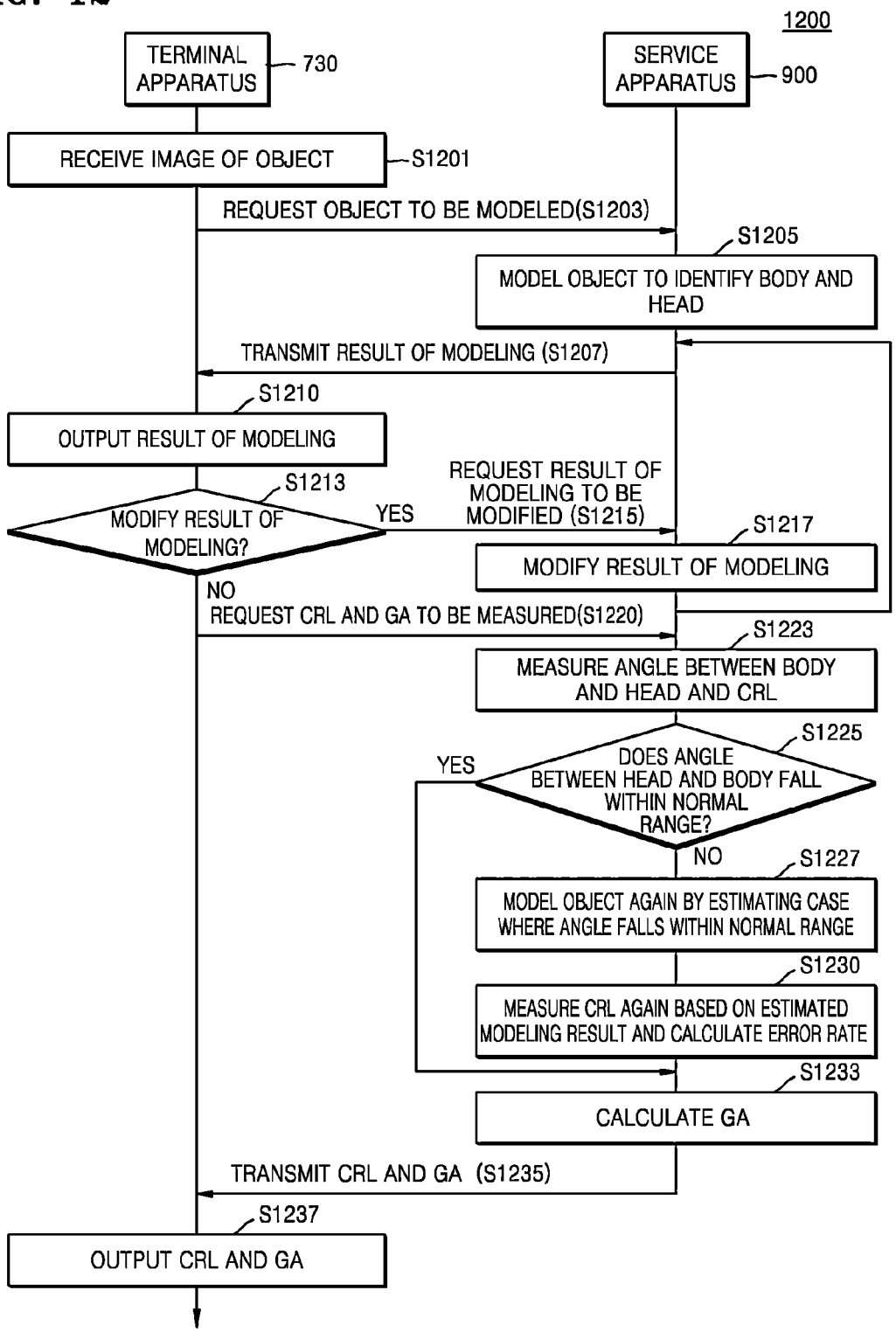
FIG. 12 is a flowchart illustrating a method of measuring a CRL of an object, according to an exemplary embodiment.

FIG. 12 is a flowchart illustrating a method 1200 of measuring a CRL of an object, according to an exemplary embodiment.

According to an exemplary embodiment, in order to measure a CRL, which is one of biometrics of an object, the object may be modeled such that a body and head of the object may be identified, and may be modeled again according to whether an angle between the body and head falls within a normal range.

Referring to FIG. 12, a terminal apparatus 730 may receive an image of an object from an external device or may read an image from a storage to measure biometrics of the object, according to a request from a user or a control signal (operation S1201). The terminal apparatus 730 may transmit the image to the service apparatus 900 to request the service apparatus 900 to model the object to measure biometrics of the object (operation S1203). The image of the object may be stored in the service apparatus 900. The terminal apparatus 730 may request the service apparatus 900 to model the image of the object stored in the service apparatus 900 and provide a result of modeling the object.

The object may be modeled such that a body and head of the object may be identified, based on the image of the object (operation S1205). A result of modeling the object may be transmitted to the terminal apparatus 730 (operation S1207). The result of modeling the object may be output to a user via the output device of the terminal apparatus 730 (operation S1210). When the user views the result of modeling the object and requests the service apparatus 900 to modify the result of modeling the object, via the input device of the terminal apparatus 730 (operations S1213 and S1215), the result of modeling the object may be modified as requested by the user (operation S1217).

If there is no request from the user to modify the result of modeling the object and the terminal apparatus 730 requests the service apparatus 900 to provide biometrics of the object (operation S1220), then the service apparatus 900 may measure biometrics of the object, based on the result of modeling the object (operation S1223).

For example, a CRL of the object may be measured based on the result of modeling the object. A GA may be calculated from the CRL. First, characteristic points on the head and body of the object may be extracted, a central axis may be set on a figure, i.e., an object model, obtained by modeling the object, based on the extracted characteristics points, and then, biometrics of the object may be measured. In operation S1223, an angle between the body and head of the object and the CRL of the object may be measured based on the central axis.

When the angle between the head and body of the object falls within the normal range, the CRL of the object may be accurately measured. In the case of a fetus, the CRL may be measured to be small when the fetus crouches down to a large extent and may be measured to be too large when the fetus stretches. Thus, the measured CRL may be not appropriate for calculating a GA, which is a value for diagnosing a state of the fetus.

Thus, whether the angle between the head and body of the object falls within the normal range may be determined based on information about the normal range of this angle, included in the biometrics data 922 stored in the storage 920 of the service apparatus 900 (operation S1225), thereby enabling the CRL to be accurately measured.

If the angle between the head and body of the object does not fall within the normal range, the object is modeled again by estimating a case where the angle falls within the normal range (operation S1227). In the case of a fetus, if the angle between the head and body of the object does not fall within the normal range since the fetus crouches down to a large extent, modeling of the object may be estimated and performed again by controlling a figure obtained by modeling the object such that the central axis on the head or body may be moved to a side and the angle may thus fall within the normal range.

A CRL of the object may be measured again based on a result of modeling the object again, and the measured CRL and the CRL measured based on the previous result of modeling the object may be compared to calculate an error rate therebetween (operation S1230).

A GA for diagnosing a state of a fetus may be calculated from the CRL (operation S1233). The CRL and/or GA may be transmitted to the terminal apparatus 730 (operation S1235) and may be output via the output device of the terminal apparatus 730 (operation S1237).

Figure 13:
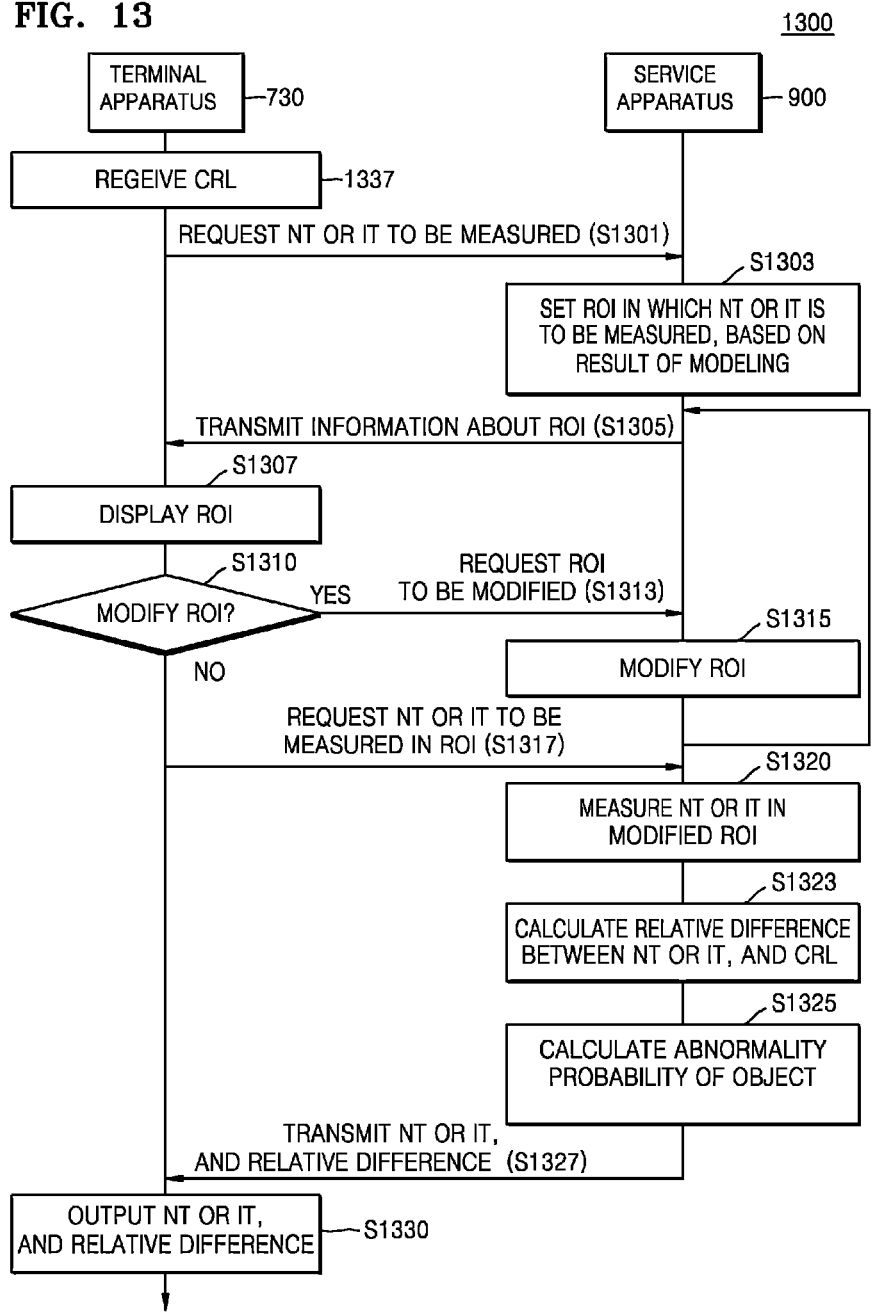
FIG. 13 is a flowchart illustrating a method of measuring an NT or an IT of an object, according to an exemplary embodiment.

FIG. 13 is a flowchart illustrating a method 1300 of measuring an NT or an IT of an object, according to an exemplary embodiment.

According to an exemplary embodiment, an IT or NT of an object may be measured based on a result of modeling the object. Thus, the object may be modeled such that the head and body of the object may be identified according to an exemplary embodiment as described above, and the IT or NT of the object may then be measured based on a result of modeling the object. Measuring a CRL may be optionally performed. For example, in operation S1337, the CRL may be received as an output of the operation S1237 of FIG. 12.

Referring to FIG. 13, locations of the NT or IT of the object may be estimated based on a result of modeling the object. In the case of a fetus, the NT is the nape and may thus be estimated as a region in which the head and body intersect, and the IT is located in the skull and may thus be estimated to be located in a region in which a central point on the head and a central axis on the head intersect. An ROI in which the NT or IT may be measured may be indicated.

First, a terminal apparatus 730 requests a service apparatus 900 to measure an NT or IT of an object and provide a result of the measuring, according to a request from a user of the terminal apparatus 730 or a control signal (operation S1301). The service apparatus 900 sets a region in which the NT or IT is to be measured, i.e., an ROI, based on a result of modeling the object (operation S1303). When the set ROI is to be verified by a user, information about the set ROI may be transmitted to the terminal apparatus 730 (operation S1305). The ROI may be displayed on the terminal apparatus 730 (operation S1307)

When the user views the displayed ROI and requests to modify the ROI, (operations S1310 and S1313), the ROI is modified as requested by the user (operation S1315). The NT or IT may be requested to be measured in the modified ROI (operation S1317), and then be measured in the modified ROI (operation S1320).

The NT and IT are measured as lengths and may thus be displayed in the form of a line, together with the ROI.

After the NT or IT is measured, a relative difference between the NT or IT and the CRL may be calculated (operation S1323). An abnormality probability of the object may be calculated using the relative difference and then be provided to the terminal apparatus 730 (operation S1325). In this case, the relative difference may be expressed as NT/CRL or IT/CRL. The CRL has to be measured to calculate the relative difference between the CRL and the NT or IT.

The measured NT and/or IT, and the relative difference between the NT or IT and the CRL may be transmitted to the terminal apparatus 730 (operation S1327), and may then be output via the output device of the terminal apparatus 730 (operation S1330).

Figure 14A:
FIGS. 14A and 14B illustrate examples of an ultrasound image of an object transmitted to a terminal apparatus or a service apparatus according to an exemplary embodiment.
Figure 14B:
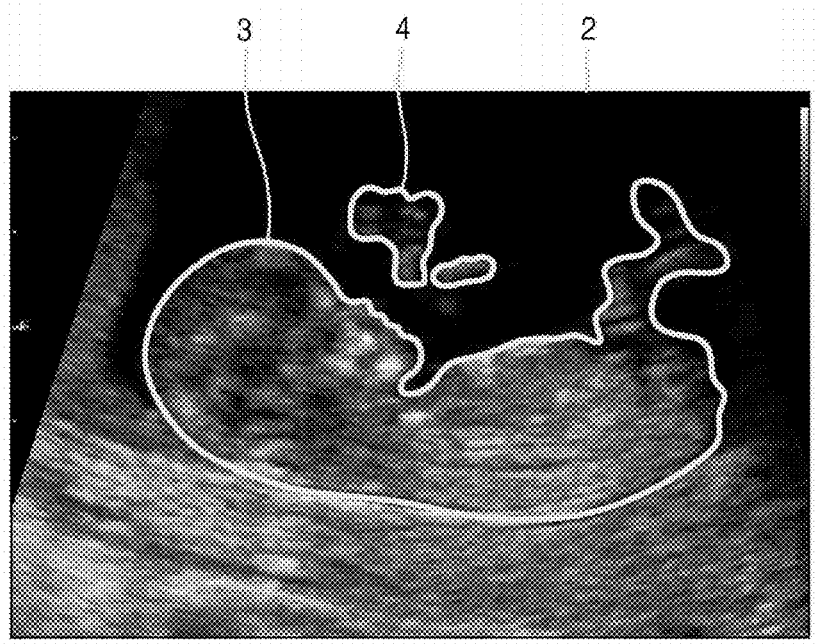

FIGS. 14A and 14B illustrate examples of an ultrasound image of an object transmitted to a terminal apparatus or a service apparatus according to an exemplary embodiment.

Specifically, FIG. 14A illustrates an example of an ultrasound image 1 of a fetus, received, for example, by the controller 120 or 220 of FIG. 1 or 2 or the service provider 830 or 930 of FIG. 8 or 9. The ultrasound image 1 includes a cross-section of the fetus, based on which biometrics of the fetus may be measured.

Referring to FIG. 14B, biometrics of the fetus may be measured by extracting portions 3 and 4 of an ultrasound image 2 of the fetus.

An object illustrated in FIG. 15 may be the same as the ultrasound image of FIG. 14A or 14B or may be obtained by extracting a part of the ultrasound image 1 or 2 of FIG. 14A or 14B.

Figure 15A:
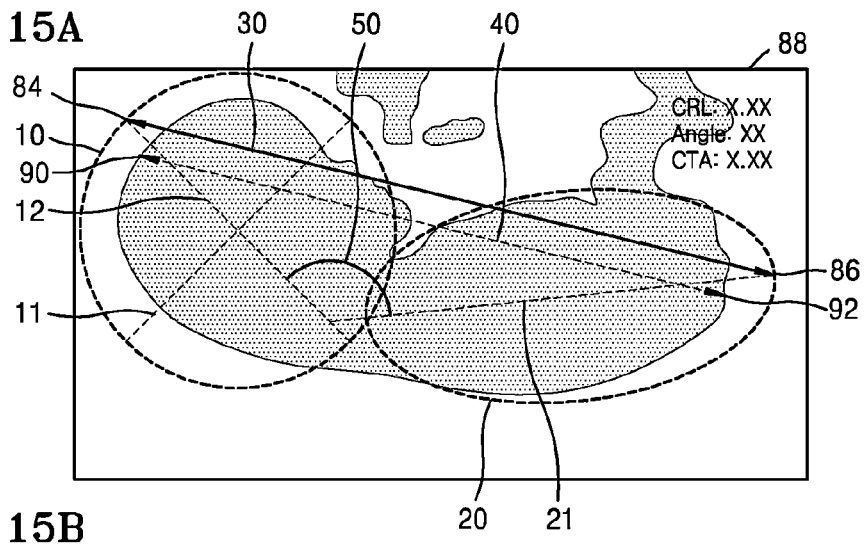
FIGS. 15A, 15B, and 15C illustrate images each showing a result of modeling an object and a result of measuring a CRL, IT, and NT of the object, according to an exemplary embodiment.
Figure 15B:
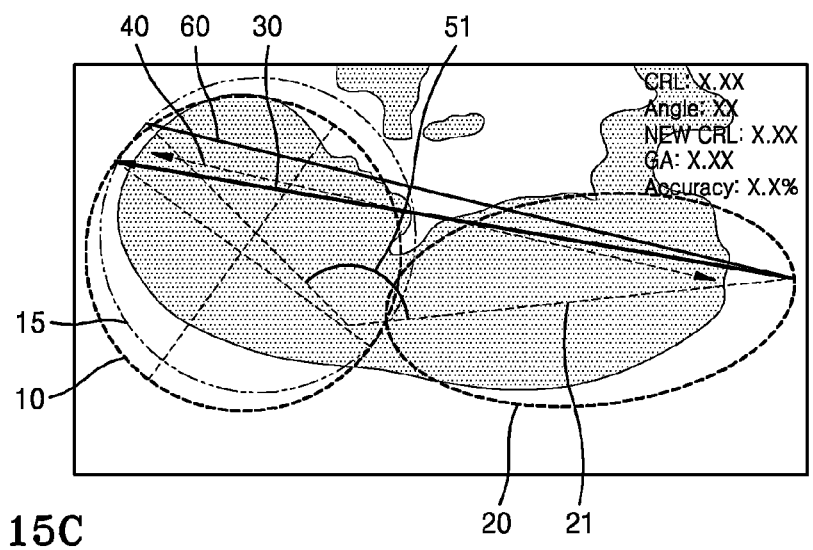
Figure 15C:
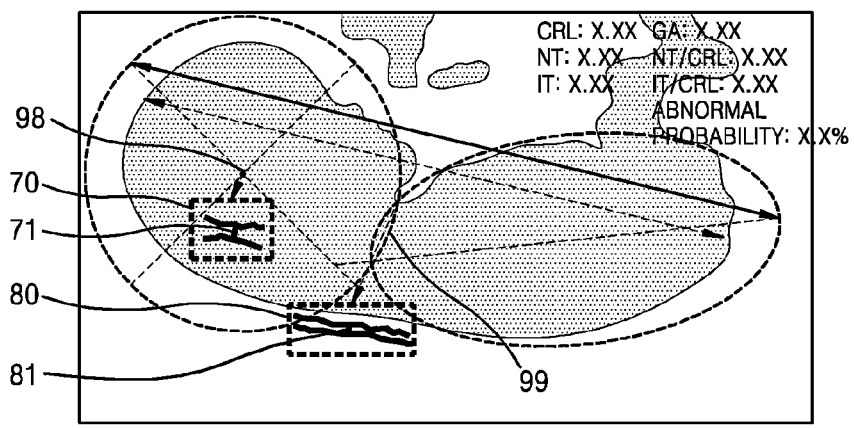

FIGS. 15A to 15C illustrate examples of modeling an object and measuring a CRL, IT, and NT of the object, according to exemplary embodiments FIG. 15A illustrates an example of a result of modeling the fetus and a result of measuring a CRL of the fetus displayed on a screen 88.

Referring to FIG. 15A, the fetus may be modeled such that the head and body are identified in a circular shape 10 and an oval shape 20, respectively, characteristic points on the head and body may be extracted, and central axes 11, 12, and 21 are then set and indicated based on the characteristic points.

A CRL 30 may be automatically displayed and measured between points 84 and 86 of the object model, based on the central axes 11, 12, and 21. A user may select desired points 90, 92 of the fetus to be measured and may manually measure a CRL 40 between the points 90, 92.

An angle 50 between the head and body may also be measured with respect to the central axes 11, 12, and 21. Whether the angle 50 falls within a normal range may be determined.

FIG. 15B illustrates an example of a result of modeling the fetus and a result of measuring a CRL of the fetus when an angle between the head and body does not fall within a normal range.

If the angle between the head and body of the object does not fall within the normal range, the object is modeled by estimating a case where the angle between the head and body falls within the normal range. Referring to FIG. 15B, if the angle falls outside the normal range, a result of modeling the head is moved toward a result of modeling the body (as indicated with a line 15) in order to adjust the angle between the head and body to fall within the normal range and a CRL of the fetus (as indicated with a line 60) is measured using the result of modeling the body including the angle 51 falling within the normal range.

FIG. 15C illustrates an example of a result of modeling the fetus and a result of measuring an IT and NT of the fetus.

The NT and IT may be measured by setting regions on the portions of the object that is modeled as ROIs.

Referring to FIG. 15C, a region around a central point 98 on the head may be set as a first ROI 70 of the IT. A region 99 in which the head and body contact each other may be set as a second ROI 80 of the NT. The first ROI 70 and the second ROI 80 may be displayed as expanded regions. Also, parts of the ROIs 70 and 80 in which the IT and NT are to be measured may be displayed as lines 71 and 81. A user may view displayed information and may directly modify the ROIs 70 and 80 or the parts of the ROIs 70 and 80 in which the IT and NT are to be measured.

Figure 16:
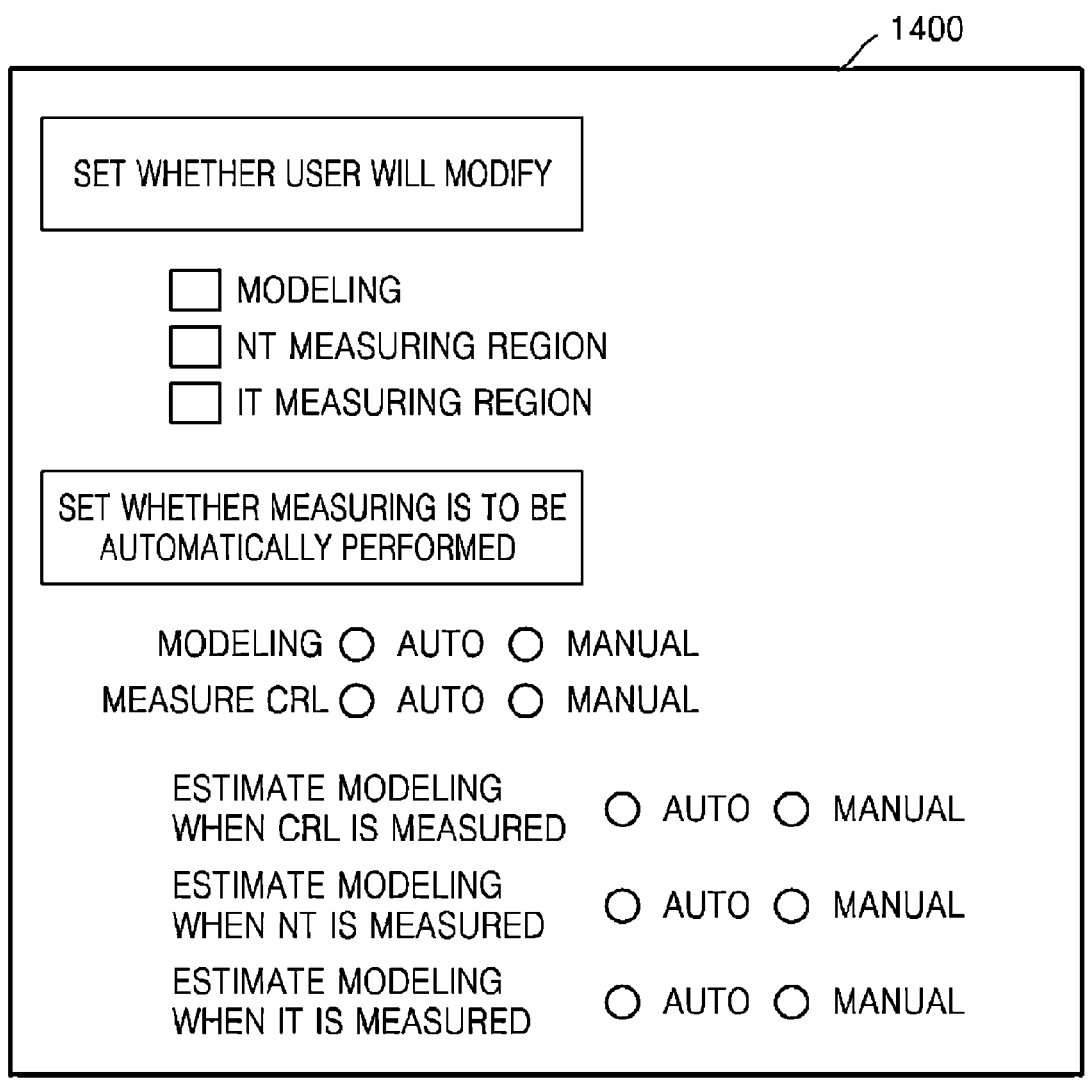
FIG. 16 illustrates a user interface screen, according to an exemplary embodiment.

FIG. 16 illustrates a screen image on which whether an object is to be modeled, whether biometrics of the object are to be automatically measured, and whether the measured biometrics are to be verified by a user after the measurement of the biometrics may be set.

Referring to FIG. 16, a user interface 1400 via which the biometrics of the object may be set to be measured after a user verifies a result of modeling the object, an NT measuring region, and an IT measuring region may be provided. If the biometrics are set to be measured after the user verifies the result of modeling the object, the NT measuring region, and the IT measuring region, then the result of modeling the object or the NT measuring region and the IT measuring unit may be automatically set and displayed, whether these displayed items are to be modified may be determined according to the user's verification, and then the biometrics of the object may be measured.

Also, after modeling of the object, the result of modeling the object, the NT measuring region, and the IT measuring region are determined, the user interface of FIG. 16 may be provided so that a user may determine whether biometrics of the object, such as a CRL, an NT, and an IT, are to be automatically or manually measured. In this case, if the biometrics of the object are determined to be automatically measured, the biometrics are measured by setting measuring regions based on a result of modeling the object. If the biometrics of the object are determined to be manually measured, the biometrics are measured by manually modeling the object or setting measuring regions by the user. For example, when the biometrics are measured by measuring lengths of portions of the object, it is possible to set such that a user may make dots on an image of the object to measure the lengths.

Exemplary embodiments can be embodied as software codes that may be read by a computer (including various devices capable of processing information), in a computer-readable recording medium. Here, the computer-readable recording medium may be any recording apparatus capable of storing data that is read by a computer system, e.g., a ROM, a RAM, a CDROM, a magnetic tape, a floppy disk, an optical data storage device, and so on.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art. Descriptions of features or aspects within each embodiment should typically be considered as available for other similar features or aspects in other embodiments.

What is claimed is:

1. A method of measuring biometrics of an object, the method comprising:
    receiving, by a processor, an ultrasound image of the object that is acquired by an ultrasound apparatus and includes a head and a body of the object, wherein the object is a fetus;
    modeling, by the processor, the object included in the ultrasound image as a first geometrical shape and a second geometrical shape identifying the head and the body of the object, respectively, and generating a modeling result;
    displaying, on a display, the first geometrical shape and the second geometrical shape around the identified head and the identified body of the object, respectively; and
    measuring, by the processor, and then displaying biometrics of the object including a crown-rump length (CRL), based on the modeling result,
    wherein the measuring the biometrics includes:
        measuring an angle between a first axis set in the first geometrical shape and a second axis set in the second geometrical shape,
        determining that the angle is outside a certain range, and
        modifying the modeling result so that the angle becomes within the certain range and measuring the biometrics of the object including the CRL based on the modified modeling result.

2. The method of claim 1, wherein the first geometrical shape and the second geometrical shape are displayed as oval shapes, respectively, and
    the modifying the modeling result comprises modifying at least one of the oval shapes based on a user input signal.

3. The method of claim 1, wherein the measuring the biometrics of the object further comprises:
    detecting a region-of-interest (ROI) for measuring the biometrics, based on the modeling result; and
    measuring the biometrics in the ROI.

4. The method of claim 3, wherein the detecting the ROI comprises:
    displaying the detected ROI to be differentiated from other portions of the object;
    displaying a region for measuring the biometrics, in the ROI; and
    modifying the ROI or the region for measuring the biometrics, according to a user input signal.

5. The method of claim 1, wherein the measuring the angle comprises:
    detecting a certain point on the head of the object;
    setting the first axis to extend through a point on the first geometrical shape of the head that corresponds to the certain point; and
    measuring an angle between the head and the body of the object as the angle between the first axis and the second axis.

6. The method of claim 1, wherein the modifying further comprises:
    displaying the modified modeling result.

7. The method of claim 1, wherein the measuring the biometrics further comprises:
    measuring at least one among a nuchal translucency (NT) and an intracranial translucency (IT) of the object; and
    calculating at least one among a first ratio between the CRL and the NT and a second ratio between the CRL and the IT,
    wherein the displaying CRL further comprises displaying at least one among the measured NT, the measured IT, the first ratio, and the second ratio.

8. The method of claim 1, wherein the first geometrical shape and the second geometrical shape are displayed as visual indicators surrounding the identified head and the identified body of the object, respectively.

9. The method of claim 1, wherein the modifying the modeling result comprises moving, by a user input on the display, at least one among the first axis and the second axis, to increase or decrease the angle between the first axis and the second axis.

10. A terminal apparatus for measuring biometrics of an object, the terminal apparatus comprising:
    a storage which stores an ultrasound image of the object that is acquired by an ultrasound apparatus and includes a head and a body of the object, wherein the object is a fetus;
    a processor; and
    software which is stored in the storage and configured to, via the processor, perform operations of:
        modeling the object included in the ultrasound image as a first geometrical shape and a second geometrical shape identifying the head and the body of the object, respectively,
        generating a modeling result,
        controlling a display to display the first geometrical shape and the second geometrical shape around the identified head and the identified body of the object, respectively, and
        measuring and then displaying the biometrics of the object including a crown-rump length (CRL), based on the modeling result,
    wherein the operation of the measuring the biometrics includes:
        measuring an angle between a first axis set in the first geometrical shape and a second axis set in the second geometrical shape,
        determining whether the angle is within a certain range, in response to the determining that the angle is within the certain range, measuring the biometrics of the object including the CRL based on the modeling result, and in response to the determining that the angle is outside the certain range, modifying the modeling result so that the angle becomes within the certain range and measuring the biometrics of the object including the CRL based on the modified modeling result.

11. The terminal apparatus of claim 10, further comprising an input device configured to receive a user input,
wherein the software is further configured to perform the operation of modifying the modeling result, based on a user input signal.

12. The terminal apparatus of claim 10, wherein the storage stores biometrics data including information about the certain range of the angle.

13. The terminal apparatus of claim 12, wherein the software is further configured to perform the operation of calculating an error rate between the biometrics measured based on the modified modeling result and the biometrics measured using the modeling result, and
wherein the error rate is output on the display.

14. The terminal apparatus of claim 10, wherein the software is further configured to perform the operations of detecting a region-of-interest (ROI) for measuring the biometrics, based on the modeling result, measuring the biometrics in the ROI, and controlling the display to output the detected ROI to be differentiated from other portions of the object, and to output a region for measuring the biometrics in the ROI.

15. The terminal apparatus of claim 14, further comprising an input device configured to receive a user input,
wherein the software is further configured to perform the operation of modifying the ROI according to a user input signal.

16. The terminal apparatus of claim 10, wherein the software is further configured to perform the operations of detecting a certain point on the head of the object, and setting the first axis to extend through a point on the first geometrical shape of the head that corresponds to the certain point.

17. The terminal apparatus of claim 16, wherein the storage stores biometrics data including information about the certain range of the angle, and
the software is further configured to perform the operation of measuring an angle between the body and the head of the object as the angle between the first axis and the second axis.

18. The terminal apparatus of claim 17, wherein the software is further configured to perform the operations of measuring at least one among a nuchal translucency (NT) and an intracranial translucency (IT) of the object, and calculating at least one among a first ratio between the CRL and the NT and a second ratio between the CRL and the IT.

19. The terminal apparatus of claim 10, wherein the software is further configured to perform the operations of detecting a region-of-interest (ROI) for measuring the biometrics, based on the modeling result, and providing a user interface which receives a user input signal indicating whether the modeling result or the detected ROI is to be viewed by a user, after the modeling the object or the detecting the ROI is automatically performed.

20. The terminal apparatus of claim 10, wherein the software is further configured to perform the operation of providing a user interface which receives a user input signal indicating whether at least one among modeling the object, extracting a region for measuring the biometrics of the object, and modifying the modeling result is to be performed automatically or manually.

21. A method comprising:
receiving, by a processor, an ultrasound image of an object that is acquired by an ultrasound apparatus and includes a head and a body of the object, wherein the object is a fetus;
segmenting, by the processor, the head and the body of the object into portions;
modeling, by the processor, the segmented portions based on an object model as a first geometrical shape and a second geometrical shape that represent the head and the body of the object, respectively, in a modeling result;
displaying, on a display, the first geometrical shape and the second geometrical shape around the head and the body of the object, respectively; and
measuring, by the processor, and then displaying biometrics of the object including a crown-rump length (CRL), based on the first geometrical shape and the second geometrical shape, by:
measuring an angle between a first axis set in the first geometrical shape and a second axis set in the second geometrical shape,
determining that the angle is outside a certain range, and
modifying the modeling result so that the angle becomes within the certain range and measuring the biometrics of the object including the CRL, based on the modified modeling result.

22. The method of claim 21, wherein the measured angle between the first axis set in the first geometrical shape and the second axis set in the second geometrical shape corresponds to an angle between the head and the body of the object in the ultrasound image.

23. The method of claim 21, further comprising:
measuring at least one among a nuchal translucency (NT) and an intracranial translucency (IT) of the object; and
calculating at least one among a first ratio between the CRL and the NT and a second ratio between the CRL and the IT.

* * * * *